US012673916B2

(12) United States Patent
Sung et al.

(10) Patent No.: US 12,673,916 B2
(45) Date of Patent: Jul. 7, 2026

(54) METHOD FOR NITRILATION REACTION OF ACRYLIC ACID ESTER

(71) Applicants:HYUNDAI MOTOR COMPANY, Seoul (KR); KIA CORPORATION, Seoul (KR); POSTECH RESEARCH AND BUSINESS DEVELOPMENT FOUNDATION, Pohang-si (KR)

(72) Inventors: Jong Geun Sung, Hwaseong-si (KR); Sung Wan Jeon, Suwon-si (KR); Da Bin Kim, Yongin-si (KR); Jeong Woo Han, Pohang-si (KR); Myeong Gon Jang, Pohang-si (KR); Byoung Joon Park, Pohang-si (KR); Yun Kyung Kim, Pohang-si (KR)

(73) Assignees: HYUNDAI MOTOR COMPANY, Seoul (KR); KIA CORPORATION, Seoul (KR); POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 672 days.

(21) Appl. No.: 18/140,899

(22) Filed: Apr. 28, 2023

(65) Prior Publication Data

US 2024/0199537 A1 Jun. 20, 2024

(30) Foreign Application Priority Data

Dec. 15, 2022 (KR) ........................ 10-2022-0175866

(51) Int. Cl.
*C07C 253/22* (2006.01)
*B01J 21/06* (2006.01)

(52) U.S. Cl.
CPC ........... *C07C 253/22* (2013.01); *B01J 21/063* (2013.01)

(58) Field of Classification Search
CPC ............................ C07C 253/22; B01J 21/063
See application file for complete search history.

(56) References Cited

U.S. PATENT DOCUMENTS

| | | |
|---|---|---|
| 2018/0346411 A1 | 12/2018 | Karp et al. |
| 2021/0253516 A1 | 8/2021 | Karp et al. |

FOREIGN PATENT DOCUMENTS

KR 2018-0092090 A 8/2018

*Primary Examiner* — Alicia L Otton
(74) *Attorney, Agent, or Firm* — MCDONNELL BOEHNEN HULBERT & BERGHOFF LLP

(57) ABSTRACT

A method for nitrilation reaction of acrylic acid ester using a metal-doped titanium dioxide ($TiO_2$) catalyst includes synthesizing a metal-doped titanium dioxide ($TiO_2$) catalyst by mixing a titanium precursor, a metal precursor and an acid solvent, and obtaining a final product by injecting a gas containing ammonia and ethyl acrylate to the catalyst.

13 Claims, 5 Drawing Sheets

Synthesize metal-doped titanium dioxide (TiO₂) catalyst by mixing titanium precursor, metal precursor, and acid solvent — S10

Obtain final product by injecting gas containing ammonia and ethyl acrylate to catalyst — S20

METHOD FOR NITRILATION REACTION OF ACRYLIC ACID ESTER

CROSS REFERENCE TO RELATED APPLICATIONS

This application claims, under 35 U.S.C. § 119(a), the benefit of priority from Korean Patent Application No. 10-2022-0175866, filed on Dec. 15, 2022, the entire contents of which are incorporated herein by reference.

BACKGROUND

(a) Technical Field

The present disclosure relates to a method for nitrilation reaction of acrylic acid ester using a titanium dioxide ($TiO_2$) catalyst.

(b) Background Art

Acrylonitrile (AN) is used as a monomer of acrylonitrile butadiene styrene (ABS) and styrene-acrylonitrile (SAN), which are polymers widely used for automobile interiors, and is used as a monomer of polyacrylonitrile (PAN) fiber, which is a precursor to polyacrylonitrile (PAN) carbon fiber with high strength used in hydrogen pressure vessels.

Meanwhile, the National Renewable Energy Laboratory (NREL) in the United States has developed a nitrilation reaction process in which acrylonitrile is synthesized by preparing ethyl acrylate from 3-hydroxyl propionic acid (3-HP), which is biomass, through dehydration and then allowing the same to react with ammonia gas. Here, the nitrilation process uses metal oxide-based catalysts such as titanium dioxide ($TiO_2$), aluminum phosphate ($AlPO_4$), etc., and shows high reactivity with an acrylonitrile synthesis yield of 90% or more.

However, the titanium dioxide ($TiO_2$) catalyst presented by NREL has a problem in that the activity of the catalyst is deteriorated due to poisoning of the catalyst surface over time, and thus has a limitation in that the reaction must be stopped every 12 to 18 hours and the catalyst must be regenerated and recharged in order to reuse the catalyst.

Against the above background, therefore, development of a catalyst having high yield and high durability for synthesizing acrylonitrile (AN) from acrylate and ammonia is required.

SUMMARY

An object of the present disclosure is to provide a method for nitrilation reaction of acrylic acid ester using a metal-doped titanium dioxide ($TiO_2$) catalyst having high yield and high durability.

The objects of the present disclosure are not limited to the foregoing. The objects of the present disclosure will be able to be clearly understood through the following description and to be realized by the means described in the claims and combinations thereof.

The present disclosure provides a method for nitrilation reaction of acrylic acid ester, including synthesizing a metal-doped titanium dioxide ($TiO_2$) catalyst by mixing a titanium precursor, a metal precursor, and an acid solvent, and obtaining acrylonitrile (AN) as a final product by injecting a gas containing ammonia and ethyl acrylate to the catalyst. The titanium precursor may include titanium(IV) isopropoxide (TTIP).

The titanium dioxide ($TiO_2$) catalyst may have an anatase structure.

The metal precursor may include magnesium (Mg) or aluminum (Al).

The metal precursor may include magnesium nitrate or aluminum nitrate.

The acid solvent may include citric acid (CA).

In the method, synthesizing the catalyst may include preparing a first mixed solution by mixing the titanium precursor and an organic solvent, preparing a second mixed solution by mixing the first mixed solution with the metal precursor and an acid solution, drying a mixture of the second mixed solution and ethylene glycol, and firing a dried product.

In the method, preparing the second mixed solution may include mixing the ethylene glycol and the metal precursor in a molar ratio of 10-15:1.

In the method, synthesizing the catalyst may include mixing the acid solvent and the metal precursor in a molar ratio of 1-3:1.

In the method, synthesizing the catalyst may include mixing the metal precursor in an amount of 0.5 to 3 wt % based on the amount of the titanium precursor used.

In obtaining the final product, the concentration of the ammonia in the gas that is injected may be 1 to 15 vol %.

In the method, obtaining the final product may be performed at a temperature of 250 to 400° C.

In the method, obtaining the final product may be performed at a gas hourly space velocity (GHSV) of 500 to 4000/hour.

The time for which a reaction yield (AN production yield) of the final product converted from ethyl acrylate is maintained at 90% or more may be 25 hours or more.

BRIEF DESCRIPTION OF THE FIGURES

The above and other features of the present disclosure will now be described in detail with reference to certain exemplary embodiments thereof illustrated in the accompanying drawings, which are given hereinbelow by way of illustration only, and thus are not limitative of the present disclosure, and wherein.

DETAILED DESCRIPTION

Figure 1:
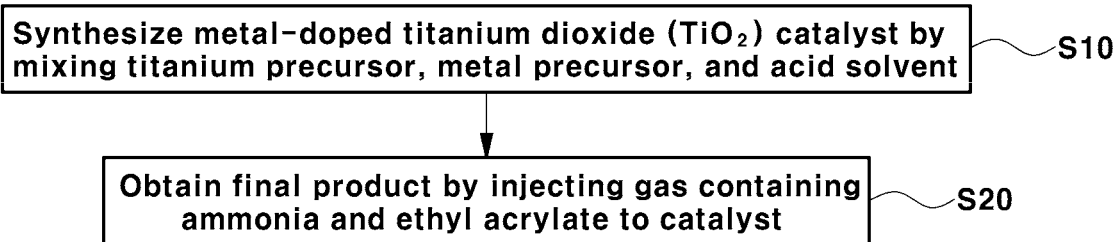
FIG. 1 is a flowchart showing a process for nitrilation reaction of acrylic acid ester according to the present disclosure.

The above and other objects, features and advantages of the present disclosure will be more clearly understood from the following preferred embodiments taken in conjunction with the accompanying drawings. However, the present disclosure is not limited to the embodiments disclosed herein, and may be modified into different forms. These embodiments are provided to thoroughly explain the disclosure and to sufficiently transfer the spirit of the present disclosure to those skilled in the art.

Throughout the drawings, the same reference numerals will refer to the same or like elements. For the sake of clarity of the present disclosure, the dimensions of structures are depicted as being larger than the actual sizes thereof. It will be understood that, although terms such as "first", "second", etc. may be used herein to describe various elements, these elements are not to be limited by these terms. These terms are only used to distinguish one element from another element. For instance, a "first" element discussed below could be termed a "second" element without departing from the scope of the present disclosure. Similarly, the "second" element could also be termed a "first" element. As used herein, the singular forms are intended to include the plural forms as well, unless the context clearly indicates otherwise.

It will be further understood that the terms "comprise", "include", "have", etc., when used in this specification, specify the presence of stated features, integers, steps, operations, elements, components, or combinations thereof, but do not preclude the presence or addition of one or more other features, integers, steps, operations, elements, components, or combinations thereof. Also, it will be understood that when an element such as a layer, film, area, or sheet is referred to as being "on" another element, it may be directly on the other element, or intervening elements may be present therebetween. Similarly, when an element such as a layer, film, area, or sheet is referred to as being "under" another element, it may be directly under the other element, or intervening elements may be present therebetween.

Unless otherwise specified, all numbers, values, and/or representations that express the amounts of components, reaction conditions, polymer compositions, and mixtures used herein are to be taken as approximations including various uncertainties affecting measurement that inherently occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

The present disclosure pertains to a method for nitrilation reaction of acrylic acid ester using a metal-doped titanium dioxide ($TiO_2$) catalyst. Hereinafter, a detailed description will be given of the present disclosure with reference to the accompanying drawings.

FIG. 1 is a flowchart showing a process for nitrilation reaction of acrylic acid ester according to the present disclosure.

With reference to FIG. 1, the method for nitrilation reaction of acrylic acid ester according to the present disclosure includes synthesizing a metal-doped titanium dioxide ($TiO_2$) catalyst by mixing a titanium precursor, a metal precursor, and an acid solvent (S10) and obtaining acrylonitrile (AN) as a final product by injecting a gas containing ammonia and ethyl acrylate to the catalyst (S20).

First, in S10, a metal-doped titanium dioxide ($TiO_2$) catalyst is synthesized.

Specifically, synthesizing the metal-doped titanium dioxide ($TiO_2$) catalyst in S10 may include preparing a first mixed solution by mixing the titanium precursor and an organic solvent, preparing a second mixed solution by mixing the first mixed solution with the metal precursor and an acid solution, drying a mixture of the second mixed solution and ethylene glycol, and firing a dried product.

In preparing the first mixed solution, the first mixed solution may be prepared by mixing a titanium precursor and an organic solvent.

Preferably, titanium(IV) isopropoxide (TTIP) is used as the titanium precursor, and ethanol is used as the organic solvent.

Also, preparing the first mixed solution may be performed with stirring at 40° C. to 70° C.

In preparing the second mixed solution, the second mixed solution may be prepared by mixing the first mixed solution with the metal precursor and an acid solution.

Here, in preparing the second mixed solution, the metal precursor may be mixed in an amount of 0.5 to 3 wt % based on the amount of the titanium precursor used.

Also, in preparing the second mixed solution, the acid solvent and the metal precursor may be mixed in a molar ratio of 1-3:1. Preferably, the acid solvent and the metal precursor are mixed in a molar ratio of 2:1.

Here, the metal precursor may include magnesium (Mg) or aluminum (Al). Preferably, magnesium nitrate or aluminum nitrate is used as the metal precursor. As the acid solvent, citric acid (CA) may be used.

Also, preparing the second mixed solution may be performed at 40° C. to 70° C.

In drying the mixture, the second mixed solution and ethylene glycol may be mixed and then dried.

In drying the mixture, ethylene glycol and the metal precursor may be mixed in a molar ratio of 10-15:1. Preferably, ethylene glycol and the metal precursor are mixed in a molar ratio of 12.5:1.

Specifically, drying the mixture may be performed by mixing ethylene glycol and then raising the temperature to about 110° C. to 120° C., followed by stirring. After completion of stirring, the temperature may be raised to about 160 to 180° C. to evaporate the internal solvent.

In firing the dried product, a metal-doped titanium dioxide ($TiO_2$) catalyst may be finally obtained. The metal-doped titanium dioxide ($TiO_2$) catalyst may have an anatase structure.

In firing the dried product, the dried product may be heat-treated at a temperature of 400° C. to 550° C. for 3 to 10 hours.

Subsequently, in S20, nitrilation reaction is performed, and in S20, a gas containing ammonia and ethyl acrylate may be injected to the titanium dioxide ($TiO_2$) catalyst to synthesize a final product. The nitrilation reaction may be carried out at a temperature of 250° C. to 400° C.

In S20, the concentration of ammonia in the gas that is injected may be 1 to 15 vol %. In S20, ammonia gas may be injected to the titanium dioxide ($TiO_2$) catalyst at a gas hourly space velocity (GHSV) of 500 to 4000/hour.

In S20, acrylonitrile may be synthesized as a final product through nitrilation reaction. The time for which the reaction yield (AN production yield) of the final product converted from ethyl acrylate is maintained at 90% or more may be 25 hours or more.

A better understanding of the present disclosure may be obtained through the following examples. These examples are merely set forth to illustrate the present disclosure, and are not to be construed as limiting the scope of the present disclosure.

Preparation Example 1 (Synthesis of Metal-Doped Catalyst)

In order to determine the optimal metal doping ratio of the $TiO_2$ catalyst used in the present disclosure, a $TiO_2$ catalyst was prepared through the following method.

50 ml of ethanol and 14.6 ml of TTIP (titanium(IV) isopropoxide, Sigma-Aldrich, >97%) were mixed at a temperature of 60° C. using a stirring bar.

Then, 0, 1, or 2.5 wt % of a metal precursor (magnesium nitrate) and citric acid (CA) were added to the mixture and a stirring process was performed. Here, the CA/metal precursor molar ratio was 2.

Then, ethylene glycol (EG) was added thereto, after which the temperature was raised to 110° C., and a stirring process was performed. Here, the EG/metal precursor molar ratio was 12.5.

Then, after sufficient stirring, the temperature was raised to 170° C. to evaporate the internal solvent. Subsequently, when the evaporated product began to harden with bubbles formed, heat treatment was performed for 5 hours in a furnace at 450° C. in an exhaust state, finally synthesizing a $TiO_2$ catalyst.

In order to determine the physical properties of the $TiO_2$ catalyst prepared in Preparation Example 1 depending on the amount of doped metal (dopant), the specific surface area and the amount of dopant were measured through BET and ICP-AES, and the results thereof are shown in Table 1 below.

TABLE 1

| Classification | $TiO_2$ | 1 wt % MDT | 2.5 wt % MDT |
|---|---|---|---|
| Specific surface area, $S_A$ (m²/g) | 80-90 | 93.1 | 135 |
| Dopant concentration (%) | — | 1.1 | 2.3 |

1 wt % MDT: 1 wt % Mg-doped $TiO_2$
2.5 wt % MDT: 2.5 wt % Mg-doped $TiO_2$
$TiO_2$: Pure $TiO_2$ having anatase structure With reference to Table 1, it was confirmed that the Mg-doped $TiO_2$ catalyst had a larger specific surface area than the pure $TiO_2$ catalyst, and also that the concentration of the dopant was similar to the amount of the precursor that was introduced during synthesis.

Based on results of EELS-mapping analysis, it was confirmed that Mg was evenly dispersed throughout the $TiO_2$ catalyst when the doped catalyst was synthesized.

Figure 2:
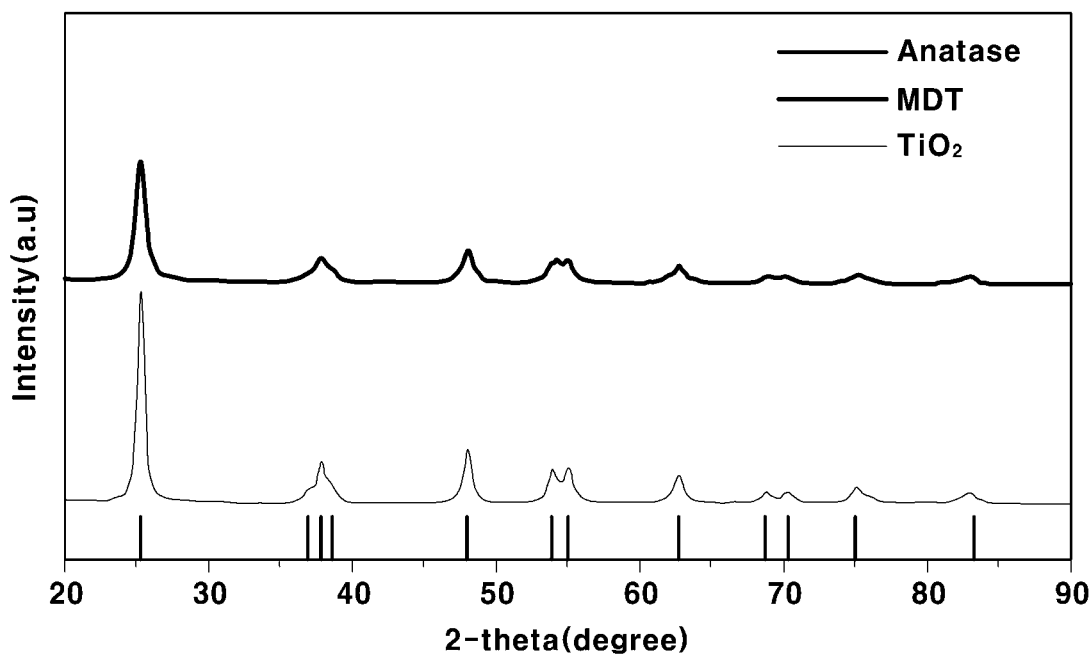
FIG. 2 shows results of XRD of a $TiO_2$ catalyst according to Preparation Example.

Also, XRD measurement was performed on the 2.5 wt % Mg-doped $TiO_2$ catalyst, and the results thereof are shown in FIG. 2. Here, FIG. 2 shows results of XRD of the $TiO_2$ catalyst according to Preparation Example.

With reference to FIG. 2, based on results of XRD, it was confirmed that both the pure $TiO_2$ and the doped catalysts had an anatase structure, and the state in which each dopant was lattice-substituted in the $TiO_2$ catalyst was confirmed through XPS.

Preparation Example 2 (TiO₂ Catalyst—Molar Ratio of Metal Precursor and Acid Solvent)

In order to determine the optimal molar ratio of the metal precursor and the acid solvent in the metal-doped $TiO_2$ catalyst, $TiO_2$ catalysts were prepared by changing the molar ratio of the metal (Mg) precursor and the acid solvent (citric acid) in Preparation Example 1.

Specifically, the $TiO_2$ catalysts were synthesized using the metal (Mg) precursor and the acid solvent (citric acid) in molar ratios shown in Table 2 below, and the BET and XRD analysis results thereof are shown in Table 2 below.

TABLE 2

| Classification | BET (m²/g) | Crystalline Size_{(101)} (nm) | Total pore volume (cm³/g) |
|---|---|---|---|
| 2.5 wt % MDT (Citric acid/Mg nitrate = 1) | 132.21 | 7.32 | 0.1443 |
| 2.5 wt % MDT (Citric acid/Mg nitrate = 2) | 134.58 | 6.83 | 0.1564 |
| 2.5 wt % MDT (Citric acid/Mg nitrate = 3) | 93.02 | 8.76 | 0.1199 |

With reference to Table 2, when citric acid was added in a molar amount twice that of the metal precursor (citric acid/Mg nitrate=2), it was confirmed that the specific surface area and pore volume were greater than those in the case of adding citric acid in an equal or three times molar amount to the metal precursor.

Figure 3:
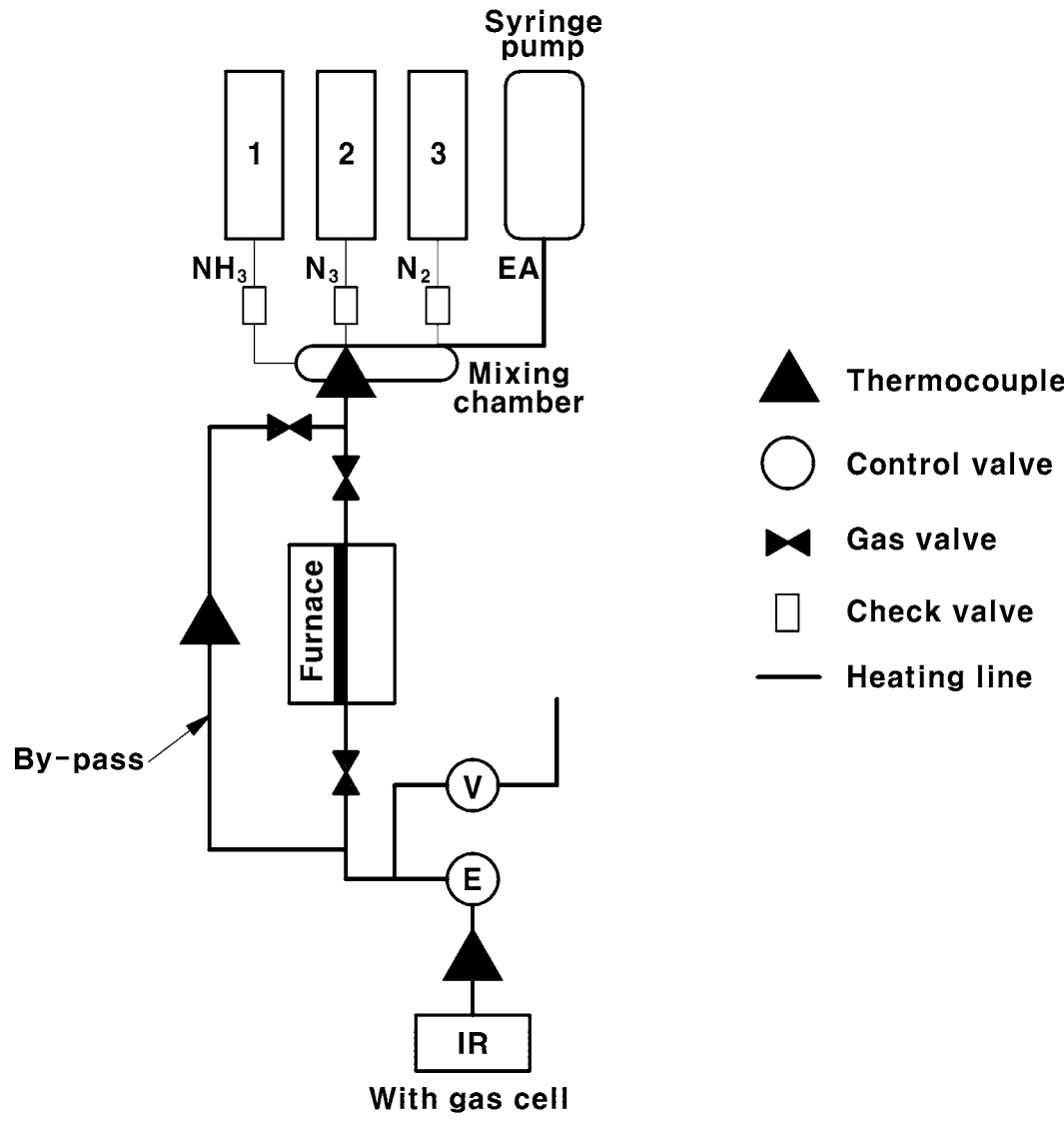
FIG. 3 schematically shows a nitrilation reaction system used in the present disclosure for nitrilation reaction.

Meanwhile, before describing nitrilation reaction, a nitrilation reaction system used in the present disclosure for such reaction is shown in FIG. 3.

With reference to FIG. 3, the nitrilation reaction system is able to control the flow rate of $N_2$ (purity of 99.999%) and $NH_3$ (10%+$N_2$ balanced) through MFC. In addition, ethyl acrylate may be injected and the flow rate thereof may be controlled using a syringe pump (50 ml). In addition, ethyl acrylate is vaporized along a heating line after passing through the syringe pump in a liquid state, and is injected into a mixing chamber (210 mm×50 mm) while maintaining a predetermined temperature (150° C.).

In the nitrilation reaction system, $N_2$ (purity of 99.999%) and $NH_3$ (10%+$N_2$ balanced) are injected into the mixing chamber through separate lines, followed by injection of the vaporized ethyl acrylate and gas mixture from the mixing chamber to the furnace (heating zone length: 200 mm, inner diameter: 65 mm). In addition, a sample holder (inner diameter: 27 mm, depth: 25 mm) filled with the catalyst may be located in the center of the furnace.

In addition, the liquid line, gas line, mixing chamber, furnace, and sample holder used in the nitrilation reaction system may be formed of SUS for corrosion prevention.

The reaction material (gas) discharged from the furnace in the nitrilation reaction system is analyzed with FTIR (Thermo-Scientific Nicolet iS20, Mercury 316SS Electropolished 10 cm Path Gas Cell).

Preparation Example 3 (Optimization of Nitrilation Reaction)

In order to confirm suitable reaction conditions when synthesizing acrylonitrile using the metal-doped titanium dioxide ($TiO_2$) catalyst, nitrilation reaction was carried out by varying the amount of $TiO_2$ catalyst and the temperature under the same reaction conditions.

Figure 4A:
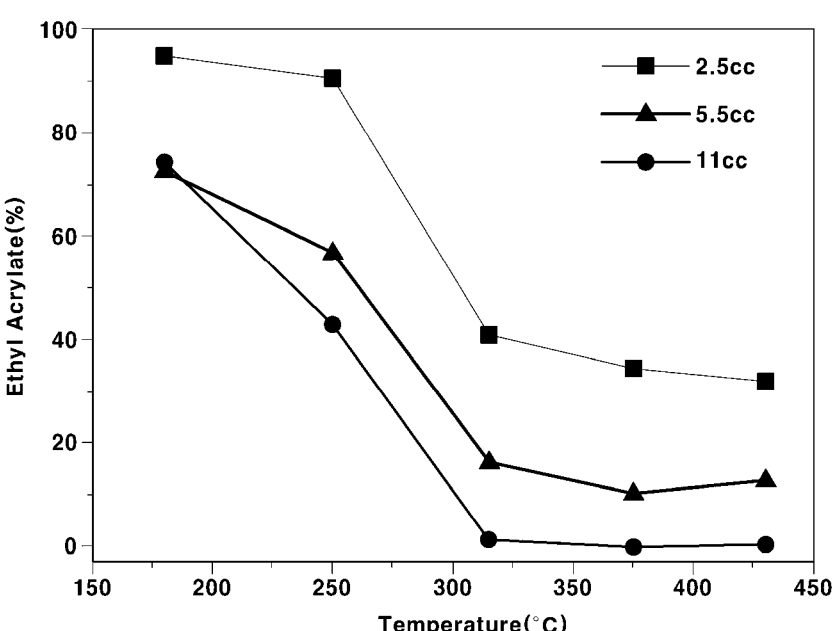
FIG. 4A shows the amount of ethyl acrylate that is decreased depending on the amount of $TiO_2$ catalyst and the temperature.
Figure 4B:
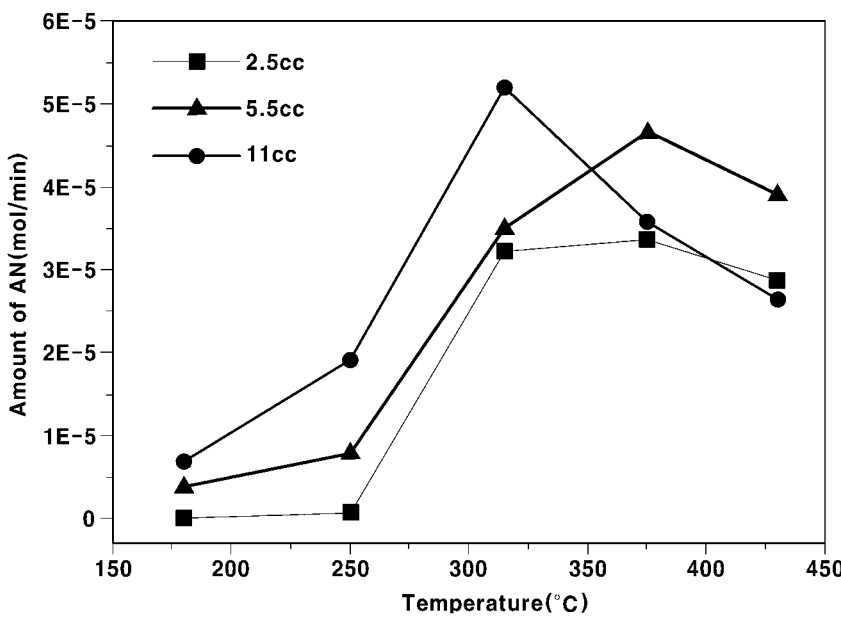
FIG. 4B shows the amount of acrylonitrile that is produced depending on the amount of $TiO_2$ catalyst and the temperature.

The results thereof are shown in FIGS. 3, 4A, and 4B.

FIG. 4A shows the amount of ethyl acrylate that is decreased depending on the amount of the $TiO_2$ catalyst and the temperature. FIG. 4B shows the amount of acrylonitrile that is produced depending on the amount of the $TiO_2$ catalyst and the temperature.

With reference to FIG. 4A, when the amount of the $TiO_2$ catalyst was increased from 2.5 cc to 11 cc, the conversion rate of ethyl acrylate was increased, and when the amount thereof was 11 cc (5.5 g), it was confirmed that the conversion rate reached about 100% at 300° C. or higher. Here, the decreased amount during reaction of ethyl acrylate as a starting material in the synthesis method represents the conversion rate. Specifically, ethyl acrylate participates in reaction as much as the amount thereof is decreased, which means that the conversion rate of ethyl acrylate increases.

With reference to FIG. 4B, it was confirmed that acrylonitrile was produced in the maximum amount when using 11 cc of the catalyst, indicating a reaction yield of 90% or more from ethyl acrylate conversion.

Therefore, in the present disclosure, when the catalyst was used in an amount of 11 cc, acrylonitrile was produced in the maximum amount at 300° C., and the amount of acrylonitrile produced (reaction yield) was decreased with an increase in the reaction temperature.

Also, in the present disclosure, when the nitrilation reaction was maintained at 400° C. or higher, the production amount was decreased after 4 hours regardless of the amount of catalyst used.

Therefore, based on the above results, the optimum temperature for nitrilation reaction was fixed at 300° C.

Next, in order to confirm the performance depending on the doped amount, $TiO_2$ catalysts were applied to nitrilation reaction and the amount of acrylonitrile (AN) produced was measured. Here, conditions for nitrilation reaction were as follows.

Reaction Conditions

GHSV: 2500 $h^{-1}$

Total flow: 458 ml/min $NH_3$: 13.8 ml/min

Ethyl acrylate: 0.0067 ml/min

Catalyst: 11 cc

Temperature: 300° C.

Figure 5:
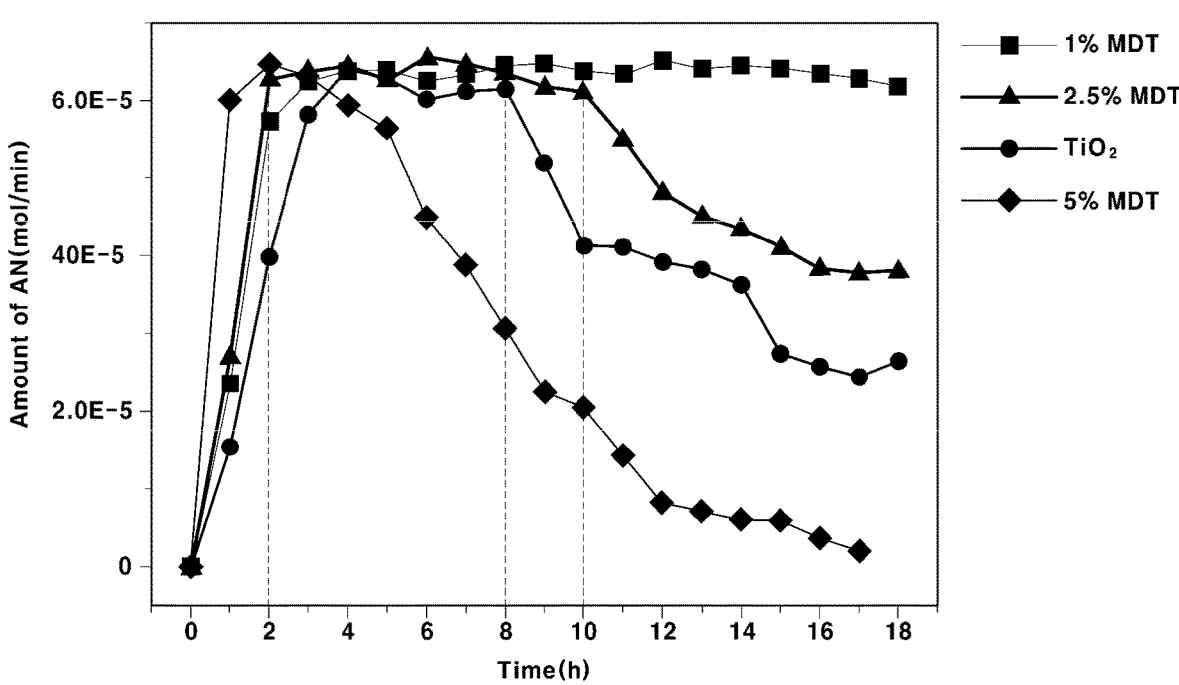
FIG. 5 is a graph showing results of measurement of the amount of acrylonitrile (AN) that is produced when the $TiO_2$ catalyst according to Preparation Example is applied to nitrilation reaction.

Specifically, $TiO_2$ catalysts were synthesized by applying the amounts and molar ratios of the titanium precursor, metal (Mg) precursor, and acid solvent (citric acid) shown in Table 3 below, and the results of measurement of the amount of acrylonitrile (AN) produced using the same are shown in Table 3 below and in FIGS. 4A and 4B. Also, FIG. 5 is a graph showing results of measurement of the amount of acrylonitrile (AN) produced when the $TiO_2$ catalyst according to Preparation Example is applied to nitrilation reaction.

TABLE 3

| Composition | | | Catalyst performance Time for which nitrilation reaction yield |
|---|---|---|---|
| Titanium(IV) isopropoxide | Magnesium nitrate | Citric acid | of 90% or more is maintained |
| 1 wt % MDT | 100 g | 1 g | 2 eq mol of Magnesium nitrate | 25 hr |
| 2.5 wt % MDT | 100 g | 2.5 g | 2 eq mol of Magnesium nitrate | 8 hr |
| 5 wt % MDT | 100 g | 5 g | 2 eq mol of Magnesium nitrate | 3 hr |

TABLE 3-continued

| Composition | | | Catalyst performance Time for which nitrilation reaction yield |
|---|---|---|---|
| Titanium(IV) isopropoxide | Magnesium nitrate | Citric acid | of 90% or more is maintained |
| Pure $TiO_2$ | 100 g | — | — | 5 hr |

1 wt % MDT: 1 wt % Mg-doped $TiO_2$
2.5 wt % MDT: 2.5 wt % Mg-doped $TiO_2$
5 wt % MDT: 5 wt % Mg-doped $TiO_2$
$TiO_2$: Pure $TiO_2$ having anatase structure With reference to Table 3 and FIG. 5, when using the 2.5 wt % Mg-doped $TiO_2$ catalyst, the highest acrylonitrile (AN) production was reached about 1 hour faster than when using the pure $TiO_2$ catalyst, and catalyst activity was maintained for about two more hours.

In addition, when the amount of Mg dopant was increased to 5 wt %, the highest acrylonitrile (AN) production was quickly reached (about 1 hour), but a catalyst deactivation phenomenon in which the amount of acrylonitrile (AN) produced was rapidly decreased was encountered.

Thus, the time for which the acrylonitrile (AN) production yield of 90% or more was maintained was about 3 hours, indicating that the catalyst activation maintenance performance was lower than that of pure $TiO_2$.

In contrast, when using the 1 wt % Mg-doped $TiO_2$, the highest acrylonitrile (AN) production was more quickly reached than when using pure $TiO_2$, and the AN production yield of 90% or more, which is the standard for maintaining catalyst activity, was maintained for 25 hours.

Therefore, based on the above results, the optimal dopant amount of the catalyst was confirmed, and the time for which the catalyst performance was maintained was confirmed to vary depending on the amount of the dopant, and thus the optimum amount of the metal dopant was determined to be 1 wt %.

Example 1

50 ml of ethanol and 14.6 ml of TTIP (titanium(IV) isopropoxide, Sigma-Aldrich, >97%) were mixed at a temperature of 60° C. using a stirring bar.

Then, 1 wt % of a metal precursor and citric acid (CA) were added to the mixture and a stirring process was performed. Here, magnesium nitrate was used as the metal precursor, and the CA/metal precursor molar ratio was 2.

Then, ethylene glycol (EG) was added thereto, after which the temperature was raised to 110° C., followed by stirring. Here, the EG/metal precursor molar ratio was 12.5.

Then, after sufficient stirring, the temperature was raised to 170° C. to evaporate the internal solvent. Subsequently, when the evaporated product began to harden with bubbles formed, heat treatment was performed for 5 hours in a furnace at 450° C. in an exhaust state, finally synthesizing a $TiO_2$ catalyst.

Example 2

A $TiO_2$ catalyst was synthesized under the same conditions as in Example 1, with the exception that aluminum nitrate was used as the metal precursor.

Comparative Example 1

A TiO$_2$ catalyst was synthesized under the same conditions as in Example 1, with the exception that cobalt nitrate was used as the metal precursor.

Comparative Example 2

A TiO$_2$ catalyst was synthesized under the same conditions as in Example 1, with the exception that the metal precursor was not used.

The physical properties of the TiO$_2$ catalysts prepared in Examples and Comparative Examples were measured using BET, and the results thereof are shown in Table 4 below.

TABLE 4

| Classification | Comparative Example 2 TiO$_2$ | Example 1 MDT | Example 2 ADT | Comparative Example 1 CDT |
|---|---|---|---|---|
| Surface area (m$^2$/g) | 80 | 93.1 | 92.5 | 77 |
| Total pore volume (%) | 0.1331 | 0.1473 | 0.1389 | 0.1325 |

MDT: Mg-doped TiO$_2$
ADT: Al-doped TiO$_2$
CDT: Co-doped TiO$_2$
TiO$_2$: Pure TiO$_2$ having anatase structure With reference to Table 4, there was no significant difference in the specific surface area and pore volume of the four catalysts.

In addition, based on results of EELS-mapping analysis, it was confirmed that each dopant was evenly dispersed throughout the TiO$_2$ catalyst when the catalyst was synthesized by the above method.

Figure 6:
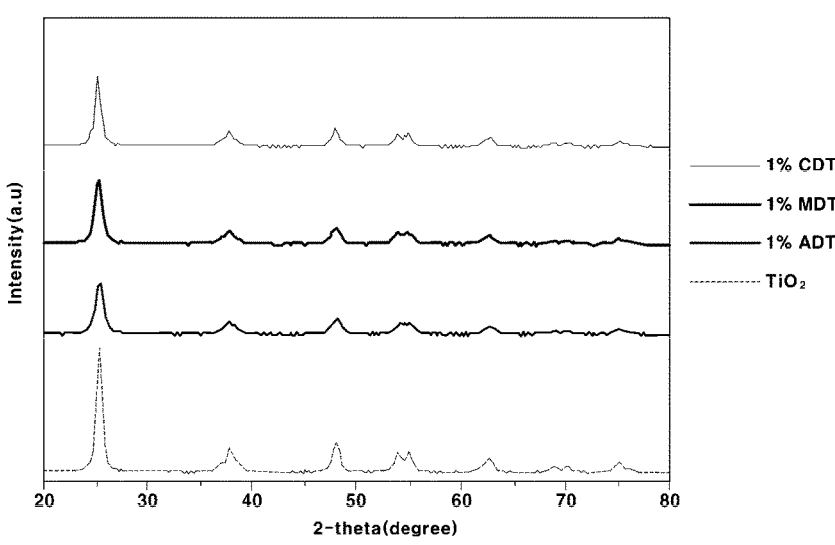
FIG. 6 shows results of XRD of $TiO_2$ catalysts according to Examples and Comparative Examples.

In addition, the physical properties of the TiO$_2$ catalysts prepared in Examples and Comparative Examples were measured through XRD, and the results thereof are shown in FIG. 6. Here, FIG. 6 shows XRD results of TiO$_2$ catalysts according to Examples and Comparative Examples.

With reference to FIG. 6, based on results of XRD analysis, it was confirmed that both the pure TiO$_2$ and the doped catalysts had an anatase structure, and the state in which each dopant was lattice-substituted in the TiO$_2$ catalyst was confirmed through XPS.

Figure 7:
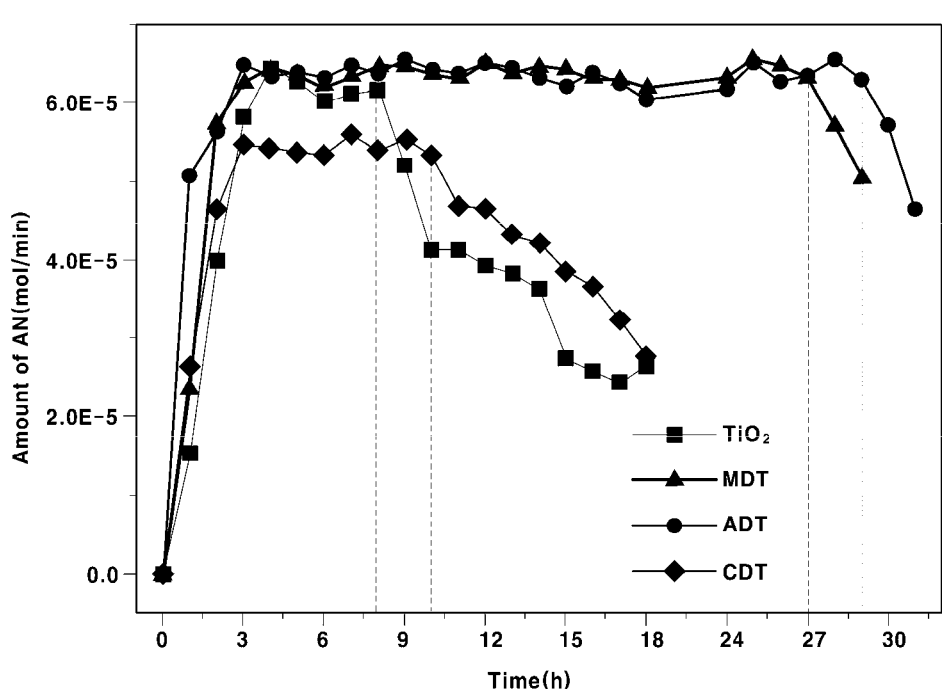
FIG. 7 is a graph showing results of measurement of the amount of acrylonitrile (AN) that is produced when the $TiO_2$ catalyst prepared in Examples and Comparative Examples is applied to nitrilation reaction.

In addition, the amount of acrylonitrile (AN) produced was measured by applying the TiO$_2$ catalysts prepared in Examples and Comparative Examples to nitrilation reaction. Here, conditions for nitrilation reaction were as follows.
Reaction Conditions
   GHSV: 2500 h$^{-1}$
   Total flow: 458 ml/min
   NH$_3$: 13.8 ml/min
   Ethyl acrylate: 0.0067 ml/min
   Catalyst: 11 cc
   Temperature: 300° C.
FIG. 7 is a graph showing results of measurement of the amount of acrylonitrile (AN) produced when the TiO$_2$ catalyst prepared in Examples and Comparative Examples is applied to nitrilation reaction.

With reference to FIG. 7, when using the pure TiO$_2$ catalyst according to Comparative Example 2, the acrylonitrile (AN) production yield reached 90% about 3 hours after reaction, and about 5 hours after reaction, the amount of acrylonitrile (AN) produced decreased rapidly.

Also, when using the Co-doped TiO$_2$ catalyst according to Comparative Example 1, it was confirmed that the activity was not good because the maximum acrylonitrile (AN) yield was low compared to when using the other catalysts.

In contrast, when using the TiO$_2$ catalyst doped with 1 wt % magnesium or aluminum according to Examples 1 and 2, the acrylonitrile (AN) production yield reached 90% about 2 hours after reaction, and the amount of acrylonitrile (AN) produced was maintained until 27 and 29 hours after reaction.

Also, it was confirmed that the effect of the titanium dioxide (TiO$_2$) catalyst doped with magnesium (Mg) or aluminum (Al) according to the present disclosure remains the same even when the catalyst is reused.

Existing TiO$_2$ catalysts are prone to catalyst deactivation in which the surface of the catalyst is poisoned (coked) owing to promotion of side reactions due to high reactivity. In this case, a catalyst regeneration process for replacing the catalyst with a new one or oxidizing and removing all the surface coking is essential. However, this process causes inefficiency in the chemical process itself and leads to an increase in production cost.

However, it was found that the TiO$_2$ catalyst doped with magnesium or aluminum in a specific amount according to the present disclosure has greatly improved catalyst safety compared to the pure catalyst.

The present disclosure is capable of obtaining a titanium dioxide (TiO$_2$) catalyst having high yield and high durability when synthesizing acrylonitrile (AN) from acrylate and ammonia.

In addition, the method for nitrilation reaction of acrylic acid ester according to the present disclosure is capable of synthesizing acrylonitrile using a titanium dioxide (TiO$_2$) catalyst doped with magnesium (Mg) or aluminum (Al), thereby enabling the time for which activation is maintained to be increased at least 5 fold compared to conventional acrylonitrile synthesis methods using a pure titanium dioxide (TiO$_2$) catalyst.

As is apparent from the above description, according to the present disclosure, a titanium dioxide (TiO$_2$) catalyst having high yield and high durability when synthesizing acrylonitrile (AN) from acrylate and ammonia can be obtained.

In addition, according to the present disclosure, acrylonitrile is synthesized using a titanium dioxide (TiO$_2$) catalyst doped with magnesium (Mg) or aluminum (Al), thereby enabling the time for which activation is maintained to be increased at least 5 fold compared to conventional acrylonitrile synthesis methods using a pure titanium dioxide (TiO$_2$) catalyst.

The effects of the present disclosure are not limited to the above-mentioned effects. It should be understood that the effects of the present disclosure include all effects that can be inferred from the description of the present disclosure.

Although specific embodiments of the present disclosure have been described with reference to the accompanying drawings, those skilled in the art will appreciate that the present disclosure may be embodied in other specific forms without changing the technical spirit or essential features thereof. Thus, the embodiments described above should be understood to be non-limiting and illustrative in every way.

The invention claimed is:
1. A method for nitrilation reaction of acrylic acid ester, comprising:
   synthesizing a metal-doped titanium dioxide (TiO$_2$) catalyst by mixing a titanium precursor comprising titanium (IV) isopropoxide (TTIP), a metal precursor comprising magnesium nitrate, and an acid solvent; and obtaining acrylonitrile (AN) as a final product by injecting a gas containing ammonia and ethyl acrylate to the catalyst.

2. The method of claim 1, wherein the titanium dioxide ($TiO_2$) catalyst has an anatase structure.

3. The method of claim 1, wherein the metal precursor further comprises magnesium (Mg) or aluminum (Al).

4. The method of claim 1, wherein the metal precursor further comprises aluminum nitrate.

5. The method of claim 1, wherein the acid solvent comprises citric acid (CA).

6. The method of claim 1, wherein the synthesizing of the catalyst comprises:

preparing a first mixed solution by mixing the titanium precursor and an organic solvent;

preparing a second mixed solution by mixing the first mixed solution with the metal precursor and an acid solution;

drying a mixture of the second mixed solution and ethylene glycol; and firing a dried product.

7. The method of claim 6, wherein preparing the second mixed solution comprises mixing the ethylene glycol and the metal precursor in a molar ratio of 10 to 15:1.

8. The method of claim 1, wherein synthesizing the catalyst comprises mixing the acid solvent and the metal precursor in a molar ratio of 1 to 3:1.

9. The method of claim 1, wherein synthesizing the catalyst comprises mixing the metal precursor in an amount of 0.5 to 3 wt % based on an amount of the titanium precursor used.

10. The method of claim 1, wherein, in the obtaining of the final product, a concentration of the ammonia in the gas that is injected is 1 to 15 vol %.

11. The method of claim 1, wherein obtaining the final product is performed at a temperature of 250° C. to 400° C.

12. The method of claim 1, wherein obtaining the final product is performed at a gas hourly space velocity (GHSV) of 500 to 4000/hour.

13. The method of claim 1, wherein a time for which a reaction yield (AN production yield) of the final product converted from ethyl acrylate is maintained at 90% or more is 25 hours or more.

* * * * *